United States Patent
Hall

(10) Patent No.: US 9,775,992 B2
(45) Date of Patent: Oct. 3, 2017

(54) IMPLANTABLE ELECTRODE

(71) Applicant: Cardiac Pacemakers, Inc., St. Paul, MN (US)

(72) Inventor: Peter Hall, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/015,882

(22) Filed: Feb. 4, 2016

(65) Prior Publication Data
US 2016/0235972 A1    Aug. 18, 2016

Related U.S. Application Data

(60) Provisional application No. 62/116,240, filed on Feb. 13, 2015.

(51) Int. Cl.
| | |
|---|---|
| *A61N 1/05* | (2006.01) |
| *A61B 5/042* | (2006.01) |
| *A61N 1/36* | (2006.01) |
| *H01J 9/02* | (2006.01) |
| *A61L 31/02* | (2006.01) |
| *C25D 11/34* | (2006.01) |
| *A61N 1/375* | (2006.01) |

(52) U.S. Cl.
CPC .......... *A61N 1/0587* (2013.01); *A61B 5/042* (2013.01); *A61L 31/022* (2013.01); *A61N 1/05* (2013.01); *A61N 1/056* (2013.01); *A61N 1/3605* (2013.01); *C25D 11/34* (2013.01); *H01J 9/02* (2013.01); *A61N 1/375* (2013.01)

(58) Field of Classification Search
CPC .......... A61N 1/05; A61N 1/056; A61B 5/042
See application file for complete search history.

(56) References Cited

U.S. PATENT DOCUMENTS

| | | |
|---|---|---|
| 3,234,110 A | 2/1966 | Beer |
| 4,003,817 A | 1/1977 | Bianchi et al. |
| 4,126,934 A | 11/1978 | Richter et al. |
| 4,156,429 A | 5/1979 | Amundson |
| 4,587,975 A | 5/1986 | Salo et al. |
| 4,677,989 A | 7/1987 | Robblee |
| 4,717,581 A | 1/1988 | Robblee |
| 4,762,136 A | 8/1988 | Baker et al. |

(Continued)

FOREIGN PATENT DOCUMENTS

| | | |
|---|---|---|
| EP | 0813885 A2 | 12/1997 |
| EP | 0813886 A2 | 12/1997 |

(Continued)

OTHER PUBLICATIONS

International Search Report and Written Opinion issued in PCT/US2016/016607, mailed Apr. 25, 2016, 11 pages.

(Continued)

*Primary Examiner* — Christopher D Koharski
*Assistant Examiner* — Natasha Patel
(74) *Attorney, Agent, or Firm* — Faegre Baker Daniels LLP

(57) ABSTRACT

An electrode for use with an implantable medical device includes an alloy and a conductive oxide layer on a surface of the alloy. The alloy includes iridium and at least one of cobalt and iron. The conductive oxide layer includes iridium oxide. The conductive oxide layer has a thickness greater than about 5 nanometers.

18 Claims, 2 Drawing Sheets

(56) References Cited

U.S. PATENT DOCUMENTS

| | | |
|---|---|---|
| 4,797,182 A | 1/1989 | Beer et al. |
| 4,919,135 A | 4/1990 | Phillips et al. |
| 4,922,607 A | 5/1990 | Doan et al. |
| 4,922,927 A | 5/1990 | Fine et al. |
| 4,944,088 A | 7/1990 | Doan et al. |
| 4,967,755 A | 11/1990 | Pohndorf |
| 5,007,435 A | 4/1991 | Doan et al. |
| 5,074,313 A | 12/1991 | Dahl et al. |
| 5,143,090 A | 9/1992 | Dutcher et al. |
| 5,156,726 A | 10/1992 | Nakada et al. |
| 5,294,317 A | 3/1994 | Saito et al. |
| 5,330,522 A | 7/1994 | Kreyenhagen |
| 5,334,293 A | 8/1994 | Cairns et al. |
| 5,368,564 A | 11/1994 | Savage |
| 5,405,373 A | 4/1995 | Petersson et al. |
| 5,464,404 A | 11/1995 | Abela et al. |
| 5,476,502 A | 12/1995 | Rubin |
| 5,507,725 A | 4/1996 | Savage et al. |
| 5,534,022 A | 7/1996 | Hoffmann et al. |
| 5,545,205 A | 8/1996 | Schulte et al. |
| 5,632,770 A | 5/1997 | Schaldach |
| 5,643,197 A | 7/1997 | Brucker et al. |
| 5,645,580 A | 7/1997 | Moaddeb et al. |
| 5,654,030 A | 8/1997 | Munshi et al. |
| 5,683,443 A | 11/1997 | Munshi et al. |
| RE35,924 E | 10/1998 | Winkler |
| 5,824,016 A | 10/1998 | Ekwall |
| 5,899,929 A | 5/1999 | Thompson et al. |
| 5,920,126 A | 7/1999 | Sohara |
| 5,935,102 A | 8/1999 | Bowden et al. |
| 5,935,160 A | 8/1999 | Auricchio et al. |
| 5,935,392 A | 8/1999 | Lubin et al. |
| 5,954,649 A | 9/1999 | Chia et al. |
| 6,006,134 A | 12/1999 | Hill |
| 6,029,091 A | 2/2000 | de la Rama et al. |
| 6,263,250 B1 | 7/2001 | Skinner |
| 6,295,474 B1 | 9/2001 | Munshi |
| 6,516,232 B2 | 2/2003 | Skinner |
| 6,677,557 B2 | 1/2004 | Ito et al. |
| 7,013,182 B1 | 3/2006 | Krishnan |
| 7,344,560 B2 | 3/2008 | Gregorich et al. |
| 7,421,299 B2 | 9/2008 | Frericks et al. |
| 2003/0215718 A1 | 11/2003 | Huang et al. |
| 2004/0220652 A1* | 11/2004 | Zhou .................. A61N 1/05 607/141 |
| 2005/0131509 A1 | 6/2005 | Atanassoska et al. |
| 2006/0035026 A1 | 2/2006 | Atanassoska et al. |
| 2007/0027532 A1* | 2/2007 | Wang .................. A61F 2/82 623/1.44 |
| 2009/0047167 A1* | 2/2009 | Gehrmann ............ C21D 6/001 420/85 |
| 2011/0014399 A1 | 1/2011 | Frericks et al. |
| 2011/0112619 A1* | 5/2011 | Foster ................ A61N 1/0575 607/127 |
| 2012/0288699 A1* | 11/2012 | Ahlberg .............. A61L 27/04 428/220 |
| 2013/0199027 A1 | 8/2013 | Singh et al. |
| 2014/0142670 A1* | 5/2014 | Radhakrishnan ....... H01J 9/02 607/116 |

FOREIGN PATENT DOCUMENTS

| | | |
|---|---|---|
| GB | 2065478 A | 7/1981 |
| WO | WO0184886 A1 | 11/2001 |

OTHER PUBLICATIONS

"U.S. Appl. No. 09/352,557 Non Final Office Action mailed Sep. 29, 2000", 10 pgs.

"U.S. Appl. No. 09/352,557 Notice of Allowance mailed Mar. 1, 2001", 7 pgs.

"U.S. Appl. No. 09/352,557 Response filed Dec. 29, 2000 to Non Final Office Action mailed Sep. 29, 2000", 8 pgs.

"U.S. Appl. No. 09/907,540 Notice of Allowance mailed Sep. 30, 2002", 8 pgs.

"U.S. Appl. No. 11/256,995 Preliminary Amendment filed Oct. 24, 2005", 6 pgs.

"U.S. Appl. No. 11/256,995, Final Office Action Mailed Jul. 17, 2009", 10 pgs.

"U.S. Appl. No. 11/256,995, Non-Final Office Action mailed Feb. 6, 2009", 8 pgs.

"U.S. Appl. No. 11/256,995, Response filed May 6, 2009 to Non Final Office Action mailed Feb. 6, 2009", 8 pgs.

Blouin et al. Activation of Ruthenium Oxide, Iridium Oxide, and Mixed Ru$_x$Ir$_{1-x}$ Oxide Electrodes during Cathodic Polarization and Hydrogen Evolution. J. Electrochem. Soc., vol. 144, No. 2, Feb. 1997. pp. 573-581.

Final Office Action issued in U.S. Appl. No. 11/256,995, mailed Jun. 9, 2010.

Robblee et al. Charge Injection Properties of Thermally-Prepared Iridium Oxide Films. Mat. Res. Soc. Symp. Proc. vol. 55. 1985, pp. 303-310.

Robblee, L.S., et al. "Activated IR: An Electrode Suitable for Reversible Charge Injection in Saline Solution." Journal of the Electrochemical Society, 130(3), (1983), 731-733.

U.S. Appl. No. 11/256,995, Advisory Action mailed Sep. 28, 2009, 3 pages.

U.S. Appl. No. 11/256,995, Non-Final Office Action mailed Dec. 30, 2009, 10 pages.

U.S. Appl. No. 11/256,995, Request for Continued Examination (RCE), filed Oct. 15, 2009, 1 page.

U.S. Appl. No. 11/256,995, Response filed Sep. 17, 2009 to Final Office Action mailed Jul. 17, 2009, 13 pages.

* cited by examiner

# IMPLANTABLE ELECTRODE

CROSS-REFERENCE TO RELATED APPLICATION

This application claims priority to Provisional Application No. 62/116,240, filed Feb. 13, 2015, which is herein incorporated by reference in its entirety.

TECHNICAL FIELD

The present invention relates to medical devices and methods for forming medical devices. More specifically, the invention relates to an electrode, an implantable device incorporating the electrode, and a method of manufacturing the electrode.

BACKGROUND

Implantable medical devices are used in a variety of therapeutic applications. In some implantable medical devices, a pulse generator and a medical lead are used together to provide electro stimulation therapy in the form of electrical pulses delivered by electrodes on the medical lead to a tissue site within a patient. Implantable electrodes may be made of alloys of precious metals such as platinum and/or palladium. Such alloys of platinum and palladium (also referred to as platinum and palladium alloys) may be corrosion resistant, biocompatible, and radiopaque. The latter characteristic enables verification during implantation that the electrode is in the proper location within the body for effective therapy delivery. However, platinum and palladium alloys are expensive. Further, platinum and palladium alloys tend to polarize during use to such an extent that the effectiveness of the medical device may be reduced.

Electrode polarization may be reduced by forming an iridium oxide coating on a surface of the electrode. Suitable iridium oxide coatings which may be formed on a platinum or palladium alloy electrodes include anodized iridium oxide films, thermal iridium oxide films, and sputtered iridium oxide films. An anodized iridium oxide film may be formed by depositing a layer of iridium on an electrode surface, and then anodizing the iridium layer in an electrolytic solution to form the iridium oxide film. The layer of iridium may be deposited by sputter deposition, which may be an expensive process that deposits much of the iridium on non-target (e.g., non-electrode) surfaces and requires sputter deposition systems that are expensive to buy and to maintain. A thermal iridium oxide film may be formed by the thermal decomposition of an iridium salt. The process may take days and the adhesion of the resulting iridium oxide film to the underlying surface may be insufficient for medical applications. A sputtered iridium oxide film is formed by direct sputter deposition of iridium oxide onto the surface by sputtering iridium in an oxygen plasma environment. As with the anodized iridium oxide film described above, the sputter deposition of the iridium oxide film may be an expensive process that deposits much of the iridium on non-electrode surfaces and requires sputter deposition systems that are expensive to buy and to maintain. The costly manufacturing operations associated with forming the iridium oxide layer contribute further to the already high cost of the electrodes made of platinum and palladium alloys. Also, subsequent processing of the electrode by, for example, welding, may remove the deposited iridium oxide film and reduce the effectiveness of the electrode.

SUMMARY

In Example 1, an electrode for an implantable medical device includes an alloy and a conductive oxide layer on a surface of the alloy. The alloy includes iridium and at least one of cobalt and iron. The conductive oxide layer includes iridium oxide and has a thickness greater than about 5 nanometers.

In Example 2, the electrode of Example 1, wherein the alloy includes the iridium in an amount from about 10 wt. % to about 60 wt. % and the balance is at least one of cobalt and iron.

In Example 3, the electrode of any of Examples 1-2, wherein the alloy includes cobalt.

In Example 4, the electrode of any of Examples 1-3, wherein the alloy further includes chromium and the conductive oxide layer further includes chromium oxide.

In Example 5, the electrode of Example 4, wherein the alloy includes the iridium in an amount from about 10 wt. % to about 50 wt. %, the chromium in an amount from about 10 wt. % to about 20 wt. %, and the balance is at least one of cobalt and iron.

In Example 6, the electrode of any of Examples 1-5, wherein the alloy further includes at least one of molybdenum in an amount not greater than about 5 wt. % and titanium in an amount not greater than about 5 wt. %.

In Example 7, the electrode of any of Examples 1-6, wherein the conductive oxide layer has a thickness between about 5 nanometers and about 2000 nanometers.

In Example 8, the electrode of any of Examples 1-7, wherein the conductive oxide layer has a thickness between about 10 nanometers and about 1000 nanometers.

In Example 9, the electrode of any of Examples 1-8, wherein the conductive oxide layer has a thickness of about 200 nanometers.

In Example 10, an implantable medical device includes a pulse generator and an elongate lead. The pulse generator includes electronic circuitry for providing electro stimulation. The elongate lead includes a proximal end connected to the pulse generator, a distal end opposite the proximal end, and at least one electrode of any of Examples 1-9. The electrode is disposed proximate to the distal end and electrically connected to the electronic circuitry.

In Example 11, the device of claim 10, wherein the implantable medical device is a cardiac function management system.

In Example 12, a method of manufacturing an electrode for use with an implantable medical device includes exposing a surface of the electrode to an electrolytic solution. The exposed electrode surface includes at least one of cobalt and iron alloyed with iridium. The method also includes applying a voltage between a cathode positioned at least partially within the electrolytic solution and the electrode to pass an electrical current between the cathode and the electrode. The method includes forming a conductive oxide layer including iridium oxide on the exposed electrode surface by reacting oxygen released from the electrolytic solution with the iridium at the exposed electrode surface.

In Example 13, the method of Example 12, wherein the electrical current is a direct electrical current, and the voltage is applied as a series of monophasic pulses.

In Example 14, the method of any of Examples 12-13, wherein the exposed electrode surface further includes chromium alloyed with the indium and at least one of cobalt and iron, and the conductive oxide layer further includes chromium oxide formed by a reaction between oxygen released from the electrolytic solution with the chromium at the exposed electrode surface.

In Example 15, the method of any of Examples 12-14, wherein the conductive oxide layer is formed until the conductive oxide layer reaches a thickness of between about 5 nanometers and about 2000 nanometers.

In Example 16, an electrode for an implantable medical device includes an alloy and a conductive oxide layer on a surface of the alloy. The alloy includes iridium and at least one of cobalt and iron. The conductive oxide layer includes iridium oxide and has a thickness greater than about 5 nanometers.

In Example 17, the electrode of Example 16, wherein the alloy includes the iridium in an amount from about 10 wt. % to about 60 wt. % and the balance is at least one of cobalt and iron.

In Example 18, the electrode of any of Examples 16-17, wherein the alloy includes cobalt.

In Example 19, the electrode of any of Examples 16-18, wherein the alloy further includes chromium and the conductive oxide layer further includes chromium oxide.

In Example 20, the electrode of Example 19, wherein the alloy includes the iridium in an amount from about 10 wt. % to about 50 wt. %, the chromium in an amount from about 10 wt. % to about 20 wt. %, and the balance is at least one of cobalt and iron.

In Example 21, the electrode of any of Examples 16-20, wherein the alloy further includes at least one of molybdenum in an amount not greater than about 5 wt. % and titanium in an amount not greater than about 5 wt. %.

In Example 22, the electrode of any of Examples 16-21, wherein the conductive oxide layer has a thickness between about 5 nanometers and about 2000 nanometers.

In Example 23, the electrode of Example 22, wherein the conductive oxide layer has a thickness between about 10 nanometers and about 1000 nanometers.

In Example 24, the electrode of Example 23, wherein the conductive oxide layer has a thickness of about 200 nanometers.

In Example 25, a method of manufacturing an electrode for use with an implantable medical device includes exposing a surface of the electrode to an electrolytic solution. The exposed electrode surface includes at least one of cobalt and iron alloyed with iridium. The method also includes applying a voltage between a cathode positioned at least partially within the electrolytic solution and the electrode to pass an electrical current between the cathode and the electrode. The method includes forming a conductive oxide layer including iridium oxide on the exposed electrode surface by reacting oxygen released from the electrolytic solution with the iridium at the exposed electrode surface.

In Example 26, the method of Example 25, wherein the electrical current is a direct electrical current, and the voltage is applied as a series of monophasic pulses.

In Example 27, the method of any of Examples 25-26, wherein the exposed electrode surface further includes chromium alloyed with the indium and at least one of cobalt and iron, and the conductive oxide layer further includes chromium oxide formed by a reaction between oxygen released from the electrolytic solution with the chromium at the exposed electrode surface.

In Example 28, an implantable medical device includes a pulse generator and an elongate lead. The pulse generator includes electronic circuitry for providing electro stimulation. The elongate lead includes a proximal end connected to the pulse generator, a distal end opposite the proximal end, and at least one electrode. The electrode is disposed proximate to the distal end and electrically connected to the electronic circuitry. The electrode includes an alloy and a conductive oxide layer on a surface of the alloy. The alloy includes iridium and at least one of cobalt and iron. The conductive oxide layer includes iridium oxide and has a thickness greater than about 5 nanometers.

In Example 29, the device of Example 28, wherein the alloy includes the iridium in an amount from about 10 wt. % to about 60 wt. % and the balance is at least one of cobalt and iron.

In Example 30, the device of any of Examples 28-29, wherein the alloy includes cobalt.

In Example 31, the device of any of Examples 28-30, wherein the alloy further includes chromium and the conductive oxide layer further includes chromium oxide.

In Example 32, the device of Example 31, wherein the alloy includes iridium in an amount from about 10 wt. % to about 50 wt. %, the chromium in an amount from about 10 wt. % to about 20 wt. %, and the balance is at least one of cobalt and iron.

In Example 33, the device of any of Examples 28-32, wherein the alloy further includes at least one of molybdenum in an amount not greater than about 5 wt. % and titanium in an amount not greater than about 5 wt. %.

In Example 34, the device of any of Examples 28-33, wherein the conductive oxide layer has a thickness between about 5 nanometers and about 2000 nanometers.

In Example 35, the device of any of Examples 28-34, wherein the implantable medical device is a cardiac function management system.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
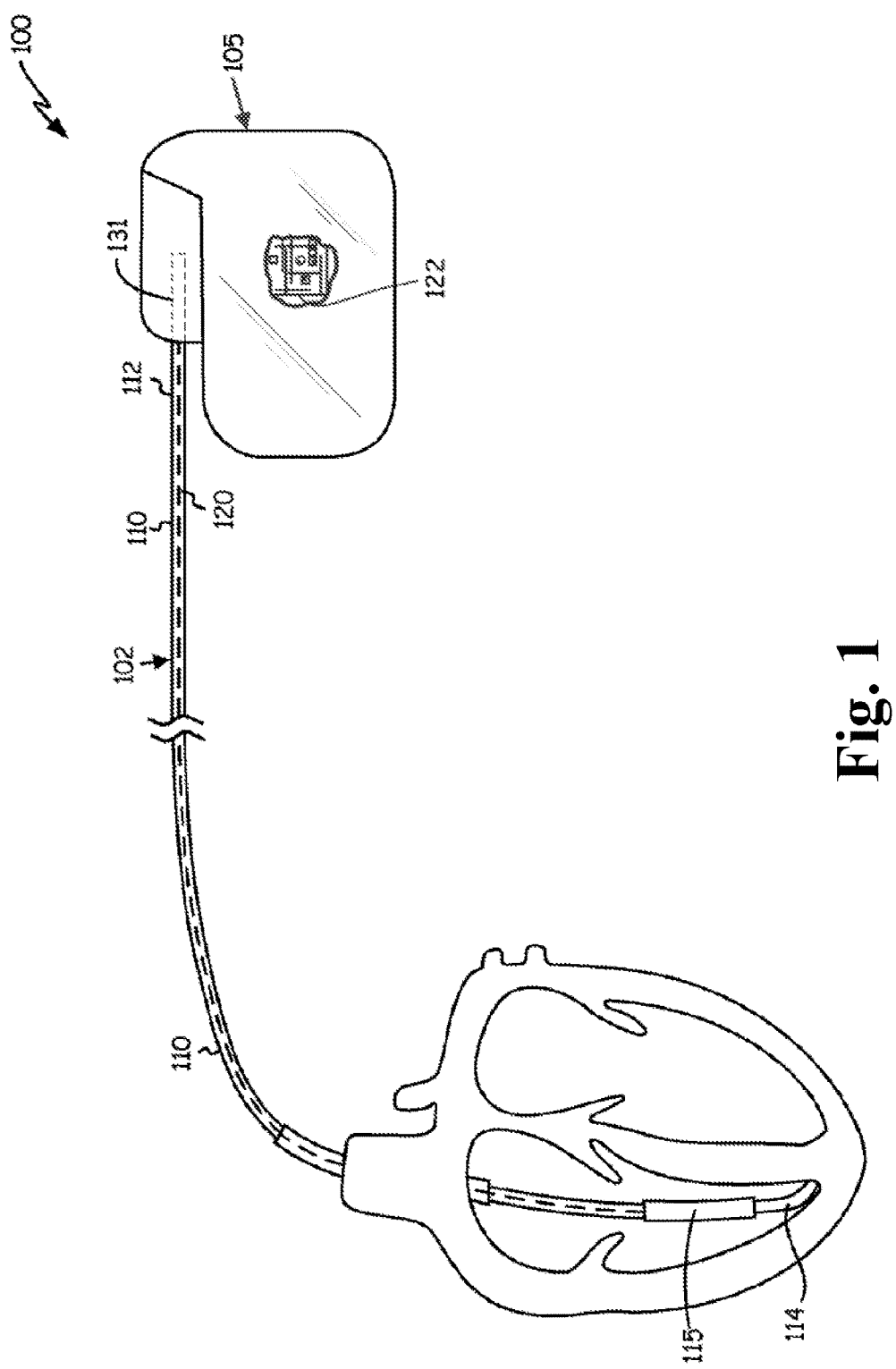
FIG. 1 illustrates an implantable medical device in accordance with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 provides an illustrative but non-limiting example of a medical application using implantable medical devices having electrodes. The application and location are illustrative only, as implantable medical devices having electrodes and incorporating embodiments of the present invention may be used in a variety of anatomical locations and for a variety of additional purposes.

FIG. 1 illustrates an implantable device 100. The implantable device 100 generically represents, but is not limited to, cardiac function management (referred to as "CFM") systems such as pacers, cardioverters/defibrillators, pacers/ defibrillators, biventricular or other multi-site resynchronization or coordination devices such as cardiac resynchronization therapy (referred to as "CRT") devices, sensing instruments, neurostimulation devices, or organ stimulation devices.

FIG. 1 illustrates that the implantable device 100 may include a lead 102 and a pulse generator 105. Lead 102 may include a lead body 110, and at least one elongate conductor 120 extending through a lumen formed within the lead body 110. The lead body 110 extends from a proximal end 112 to a distal end 114. The proximal end 112 of the lead 102 is electrically coupled with the pulse generator 105, for example, with a terminal pin 131.

The pulse generator 105 may include a source of power (not shown) as well as electronic circuitry 122. In some embodiments, the pulse generator 105 can be powered by one or more batteries, though any other internal or external power source may be used for the given application. In some embodiments, the electronic circuitry 122 can include one or more microprocessors that provide processing and/or evaluation functions, and that can determine and deliver electrical shocks or pulses of different energy levels and timing. The pulse generator can be employed as part of a variety of useful therapies, including for neurostimulation or ventricular defibrillation or cardioversion. It can also be used to pace the heart in response to one or more sensed cardiac arrhythmia including fibrillation, cardiac resynchronization, tachycardia, or bradycardia.

The lead 102 may further include one or more electrodes 115. The one or more electrodes 115 are each electrically coupled with the at least one conductor 120. The electrode 115 allows for electrical therapy, such as an electrical shock or pulse, to be delivered from the pulse generator 105 to the target tissue or location. In some embodiments, the electrode 115 also allows the pulse generator 105 to sense intrinsic signals of the heart, and generate a series of timed electrical discharges.

Figure 2:
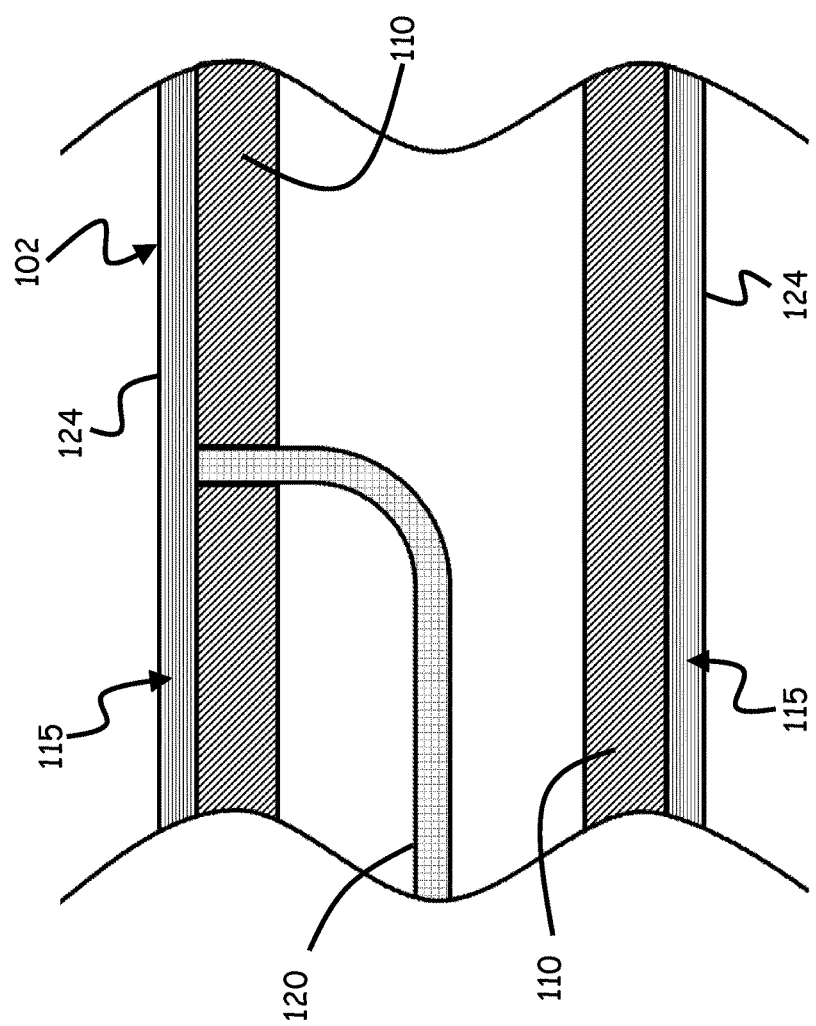
FIG. 2 is a schematic axial cross-sectional view of a portion of the implantable medical device of FIG. 1.

FIG. 2 is a schematic axial cross-sectional view of a portion of the implantable medical device of FIG. 1 illustrating an electrode in accordance with embodiments of the present invention. The electrode 115 is illustrated as a ring electrode that encompasses a circumference of, and extends partially along, the lead body 110. However, the conductor may have any suitable size and/or shape. The elongate conductor 120 connects to the electrode 115 through the lead body 110. As shown in FIG. 2, the electrode 115 includes a conductive oxide layer 124 formed on an exposed surface of the electrode 115.

In some embodiments, the electrode 115 may be formed of an alloy including iridium and at least one of cobalt and iron. In some embodiments, the electrode 115 does not include platinum or palladium except as possible contaminants in trace amounts. That is, in some embodiments, platinum and palladium are not intentionally added to the alloy. In some embodiments, the electrode 115 may additionally or alternatively be nickel-free. Nickel-free means that no nickel is intentionally added, although it may be present in trace amounts due to the difficulty in separating nickel and cobalt. As used herein, trace amounts means not more than 1.0 wt. %.

In some embodiments, the electrode 115 may be formed of an alloy including iridium in an amount as little as about 10 wt. %, about 15 wt. %, or about 20 wt. %, or as great as about 30 wt. %, about 40 wt. %, about 50 wt. %, or about 60 wt. % or may be present within any range defined between any pair of the foregoing values; and the balance at least one of cobalt and iron, or combinations thereof. For example, in some embodiments, the electrode 115 may be formed of an alloy including iridium in an amount from about 10 wt. % to about 60 wt. %, and the balance cobalt, and in other embodiments, the electrode 115 may be formed of an alloy including iridium in an amount from about 10 wt. % to about 60 wt. %, and the balance iron; and in still other embodiments, the electrode 115 may be formed of an alloy including iridium in an amount from about 10 wt. % to about 60 wt. %, and the balance a combination of cobalt and iron.

In some embodiments, the electrode 115 may be formed of an alloy including iridium in an amount as little as about 10 wt. %, about 15 wt. %, or about 20 wt. %, or as great as about 30 wt. %, about 35 wt. %, about 40 wt. %, about 45 wt. %, or about 50 wt. % or may be present within any range defined between any pair of the foregoing values; chromium in an amount as little as about 10 wt. %, about 12 wt. %, or about 14 wt. %, or as great as about 16 wt. %, about 18 wt. %, or about 20 wt. % or may be present within any range defined between any pair of the foregoing values; and the balance at least one of cobalt and iron, or combinations thereof. For example, in some embodiments, the electrode 115 may be formed of an alloy including iridium in an amount from about 10 wt. % to about 50 wt. %, chromium in an amount from about 10 wt. % to about 20 wt. %, and the balance cobalt; and in other embodiments, the electrode 115 may be formed of an alloy including iridium in an amount from about 10 wt. % to about 50 wt. %, chromium in an amount from about 10 wt. % to about 20 wt. %, and the balance iron. In some embodiments, the presence of chromium may increase corrosion resistance.

In some embodiments, the electrode 115 may be formed of an alloy including iridium in an amount as little as about 10 wt. %, about 15 wt. %, or about 20 wt. %, or as great as about 30 wt. %, about 40 wt. %, about 50 wt. %, or about 60 wt. % or may be present within any range defined between any pair of the foregoing values; at least one of molybdenum in an amount not greater than about 2 wt. %, about 4 wt. % or about 5 wt. % and titanium in an amount not greater than about 2 wt. %, about 4 wt. % or about 5 wt. %; and the balance at least one of cobalt and iron, or combinations thereof. For example, in some embodiments, the electrode 115 may be formed of an alloy including iridium in an amount from about 10 wt. % to about 60 wt. %, and at least one of molybdenum in an amount not greater than about 5 wt. % and titanium in an amount not greater than about 5 wt. %, and the balance cobalt; and in other embodiments, the electrode 115 may be formed of an alloy including iridium in an amount from about 10 wt. % to about 60 wt. %, and at least one of molybdenum in an amount not greater than about 5 wt. % and titanium in an amount not greater than about 5 wt. %, and the balance iron. In some embodiments, the presence of molybdenum and/or titanium may increase corrosion resistance.

In some embodiments, the conductive oxide layer 124 includes iridium oxide. As described herein, in some embodiments, the conductive oxide layer 124 may be formed by a chemical reaction between oxygen and the iridium of the alloy. In some embodiments, the thickness of the conductive oxide layer 124 is greater than about 5 nanometers. In some embodiments, the conductive oxide layer 124 may have a thickness as little as about 10 nanometers, about 20 nanometers, about 50 nanometers, about 100 nanometers, or about 200 nanometers, or as great as about 200 nanometers, about 300 nanometers, about 400 nanometers, about 500 nanometers, about 600 nanometers, about 700 nanometers, about 800 nanometers, about 1000 nanometers, about 1500 nanometer, or about 2000 nanometers, or may have thickness within any range defined between any pair of the foregoing values. In some embodiments, the thickness of the conductive oxide layer 124 may be between about 5 nanometers and about 2000 nanometers, between about 10 nanometers and about 1000 nanometers, or between about 100 nanometers and about 300 nanometers. In other embodiments, the thickness of the conductive oxide layer 124 may be about 200 nanometers. The thickness of the conductive oxide layer 124 may be determined by measurement of the depth to which oxides of the conductive oxide layer 124 dominate and below which metallic materials dominate. The measurement may be done by, for example, cross-sectional view via a scanning electron microscope, Auger electron spectroscopy, x-ray photoelectron spectroscopy, or any other analysis technique able to detect and measure a transition from oxides to metals.

In some embodiments, the conductive oxide layer 124 may include both iridium oxide and chromium oxide. In such embodiments, the conductive oxide layer 124 may be formed by a chemical reaction between oxygen and both the iridium and the chromium of the alloy. In such embodiments, the corrosion protection of the electrode 115 provide by the conductive oxide layer 124 may be improved over embodiments not including chromium oxide in the conductive oxide layer 124.

In some embodiments, the electrode 115 may be manufactured by anodization of the indium alloy including iridium and at least one of cobalt and iron. The electrode 115 may be immersed in an electrolytic solution such that a surface of the electrode 115 is exposed to the electrolytic solution. A cathode may also be positioned within the electrolytic solution and a voltage may be applied between the cathode and the electrode 115 to pass an electrical current between the cathode and the electrode 115. The voltage may be applied as a pulsed waveform. Oxygen is released when the voltage is applied. The released oxygen reacts with the iridium of the alloy to form at least a portion of the conductive oxide layer 124 on the surface of electrode 115 exposed to the electrolytic solution. In some embodiments, the electrical current may be a direct electrical current. In other embodiments, the electrical current may be alternating current. In some embodiments, the voltage may be applied as a series of monophasic pulses. In other embodiments, the voltage may be applied as a series of biphasic pulses.

The conductive oxide layer 124 is formed by anodization of the alloy forming electrode 115. That is, the conductive oxide layer 124 is not formed by depositing an iridium layer followed by anodization.

In some embodiments, the electrode 115 including the conductive oxide layer 124 formed by anodization of the alloy including iridium and at least one of cobalt and iron may exhibit electrode polarization levels less than 0.02 volts/second as measured by a voltage decay rate test or less than 0.01 volts as measured by an after-potential test, both described below in Example 1. Electrode polarization may reduce the effectiveness of an implantable medical device in several ways. For example, in applications where the pulse generator 105 relies on the electrode 115 to sense intrinsic signals of the heart so that a series of timed electrical discharges may be generated, the electrode polarization may interfere with the ability of the electrode 115 to sense such signals. Additionally or alternatively, electrode polarization may increase the total charge injection required to effectively provide therapy, depleting battery power faster than desired. Further, the increase in charge may be detrimental to the tissue itself due to possible generation of unwanted reaction byproducts.

In some embodiments, the conductive oxide layer 124 may provide corrosion protection of the electrode 115. In some embodiments, the conductive oxide layer 124 sufficiently adheres to the surface of the electrode 115. Because the oxide layer 124 is formed by oxidation of the alloy of the electrode 115 itself, there is no intervening deposited layer and the adhesion between the oxide layer 124 and the electrode may be greater than if the oxide layer was formed by first depositing a coating layer followed by anodization.

In some embodiments, the electrode 115 may be biocompatible and radiopaque. Biocompatibility may be further enhanced when the electrode 115 is nickel-free. Electrode radiopacity, or the degree to which an electrode may be radiopaque, may be evaluated by ASTM F640-12, entitled "Standard Test Methods for Determining Radiopacity for Medical Use." Radiopacity is a function of atomic number and density. The atomic number and the density of iridium are nearly the same as platinum and are greater than palladium, two highly radiopaque materials. Embodiments may include an iridium content sufficient to provide radiopacity. For example, embodiments having at least about 10% iridium when the balance is at least one of cobalt and iron are expected to provide the electrode 115 with radiopacity sufficient for use in the implantable electrical device 100.

The electrode 115 may provide significant cost savings over current electrodes. Iridium, cobalt and iron are historically all significantly less expensive than precious metals, such as platinum and palladium. Embodiments having no greater than about 50% iridium may result in sufficient material cost savings when compared to current electrodes. Additional cost savings may be achieved by forming the conductive oxide layer directly from the alloy of iridium and at least one of cobalt and iron directly because no sputter deposition operations are necessary.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

EXAMPLES

The following Examples are illustrative and not intended to be limiting.

Metal Sample Preparation

A plurality of metal samples containing various amounts of iridium (Ir), cobalt (Co), iron (Fe), and chromium (Cr) were prepared according to Table 1 below. Each sample was made using an electric arc melting system with a water-cooled copper hearth and an argon shielding gas. Samples 1-12 represent electrodes in accordance with embodiments of the present invention. Samples 13 and 14 are control samples of cobalt and iron, respectively.

TABLE 1

| | Weight Percent (wt. %) | | | |
|---|---|---|---|---|
| Sample | Ir | Co | Fe | Cr |
| 1 | 10 | balance | 0 | 0 |
| 2 | 20 | balance | 0 | 0 |
| 3 | 30 | balance | 0 | 0 |
| 4 | 40 | balance | 0 | 0 |
| 5 | 50 | balance | 0 | 0 |
| 6 | 10 | 0 | balance | 0 |
| 7 | 20 | 0 | balance | 0 |
| 8 | 30 | 0 | balance | 0 |
| 9 | 40 | 0 | balance | 0 |
| 10 | 50 | 0 | balance | 0 |
| 11 | 30 | balance | 0 | 20 |
| 12 | 30 | balance | 0 | 10 |
| 13 | 0 | balance | 0 | 0 |
| 14 | 0 | 0 | balance | 0 |

Oxide Layer Formation

An oxide layer was formed by a process of anodization. Each metal sample was immersed in a phosphate buffered saline electrolyte at a concentration of about 1.5 grams per liter and connected as the anode in a direct current circuit. A carbon graphite rod was also immersed in the saline electrolyte and connected as the cathode. The DC power supply of the circuit generated the required current density. The waveform employed was a current-controlled with monophasic pulses of 20 milliAmperes for 4 milliseconds, with a pause of 0.5 milliseconds between pulses. The voltage applied was between about 2 volts to about 3 volts. The anodization process was performed for an oxidation time as reported in Table 2 for each sample. The anodization process was performed at room temperature (e.g., about 20° C.).

TABLE 2

| Sample | Oxidation Time (seconds) |
|---|---|
| 1 | 20 |
| 2 | 45 |
| 3 | 20 |
| 4 | 15-20 |
| 5 | N/A |
| 6 | 60 |
| 7 | 60 |
| 8 | 60 |
| 9 | 60 |
| 10 | N/A |
| 11 | 30 |
| 12 | 30 |
| 13 | 60 |
| 14 | 60 |

Example 1

Electrode Polarization Test

Electrode polarization was evaluated by a voltage decay rate test and an after-potential test. Both tests measure how quickly an electrode voltage decays after an electrical pulse. A faster decay means reduced electrode polarization and better electrode performance.

Voltage Decay Rate Test

The voltage decay rate test (dV/dt test) measures the rate of relaxation of the electrode voltage within a specific time period following an electrical pulse. The rate of relaxation was measured over a period from 23.5 to 28.5 milliseconds following an electrical pulse. For comparison, the dV/dt test was run on each sample before and after formation of the oxide layer. The test results are shown in Table 3 below. Samples 1-4, 6-9, and 11-12 exhibited dV/dt test values below 0.02 volts/second. The control samples 13 and 14 exhibited significantly higher dV/dt test values than samples 1-4, 6- 9, and 11-12.

After-Potential Test

The after-potential test (AP test) measures the remaining potential at a specific point in time following an electrical pulse. The remaining potential was measured 10 milliseconds following an electrical pulse. For comparison, the AP test was run on each sample before and after formation of the oxide layer. The AP test results are also shown in Table 3 below. Samples 1-4, 6-9, and 11-12 exhibited AP test values below 0.10 volts. The control samples 13 and 14 exhibited higher AP test values.

TABLE 3

| | dV/dt Test (volts/second) | | AP Test (volts) | |
|---|---|---|---|---|
| Sample | Before | After | Before | After |
| 1 | 1.737 | 0.006 | 0.079 | 0.002 |
| 2 | 1.318 | 0 | 0.054 | 0.002 |
| 3 | 1.443 | 0 | 0.055 | 0.002 |
| 4 | 1.376 | 0 | 0.055 | 0.002 |
| 5 | N/A | N/A | N/A | N/A |
| 6 | 0.318 | 0 | 0.016 | 0.005 |
| 7 | 0.258 | 0 | 0.014 | 0.005 |
| 8 | 0.348 | 0 | 0.017 | 0.006 |
| 9 | 0.489 | 0.013 | 0.022 | 0.002 |
| 10 | N/A | N/A | N/A | N/A |
| 11 | 2.02 | 0.01 | 0.083 | 0.003 |
| 12 | 1.7 | 0.002 | 0.079 | 0.006 |
| 13 | 2.15 | 1.869 | 0.104 | 0.089 |
| 14 | 1.01 | 0.275 | 0.052 | 0.014 |

Example 2

Cyclic Potentiodynamic Polarization Corrosion Test

Corrosion testing of the samples was evaluated according the procedures of ASTM F2129-08, entitled "Standard Test Method for Conducting Cyclic Potentiodynamic Polarization Measurements to Determine the Corrosion Susceptibility of Small Implant Devices." The test results are also shown in Table 4 below. Corrosion was visible for samples 1, 4, 9, and 10. No corrosion was visible for samples 11 and 12, which included iridium, cobalt, and chromium.

TABLE 4

| Sample | Break-down Potential | Visible Corrosion |
|---|---|---|
| 1 | None | Observed |
| 2 | | |
| 3 | | |
| 4 | 250 mV | Observed |
| 5 | | |
| 6 | | |
| 7 | | |
| 8 | | |
| 9 | None | Observed |
| 10 | None | Observed |
| 11 | None | None |
| 12 | None | None |
| 13 | | |
| 14 | | |

I claim:

1. An electrode for use with an implantable medical device, the electrode comprising:
   an alloy consisting of:
      iridium;
      at least one of cobalt and iron; and
      optionally, chromium; and
   a conductive oxide layer on a surface of the alloy, the conductive oxide layer having a thickness between 5 nanometers and 2,000 nanometers, the conductive oxide layer consisting of iridium oxide and, optionally, chromium oxide.

2. The electrode of claim 1, wherein the alloy includes the iridium in an amount from 10 wt. % to 60 wt. % and the balance is at least one of cobalt and iron.

3. The electrode of claim 1, wherein the alloy includes cobalt.

4. The electrode of claim 1, wherein the alloy includes chromium and the conductive oxide layer includes chromium oxide.

5. The electrode of claim 4, wherein the alloy includes the iridium in an amount from 10 wt. % to 50 wt. %, the chromium in an amount from 10 wt. % to 20 wt. %, and the balance is at least one of cobalt and iron.

6. The electrode of claim 1, wherein the conductive oxide layer has a thickness between 10 nanometers and 1000 nanometers.

7. The electrode of claim 6, wherein the conductive oxide layer has a thickness of 200 nanometers.

8. An implantable medical device comprising:
   a pulse generator including electronic circuitry for providing electro stimulation; and
   an elongate lead, the lead including:
      a proximal end connected to the pulse generator;
      a distal end opposite the proximal end; and
      at least one electrode disposed proximate to the distal end and electrically connected to the electronic circuitry, the at least one electrode including:
         an alloy consisting of:
            iridium;
            at least one of cobalt and iron; and
            optionally, chromium; and
         a conductive oxide layer on a surface of the alloy, the conductive oxide layer having a thickness between 5 nanometers and 2,000 nanometers, the conductive oxide layer consisting of iridium oxide and, optionally, chromium oxide.

9. The device of claim 8, wherein the alloy is nickel-free and the alloy includes the iridium in an amount from 10 wt. % to 60 wt. % and the balance is at least one of cobalt and iron.

10. The device of claim 8, wherein the alloy includes cobalt.

11. The device of claim 8, wherein the alloy includes chromium and the conductive oxide layer includes chromium oxide.

12. The device of claim 11, wherein the alloy includes iridium in an amount from 10 wt. % to 50 wt. %, the chromium in an amount from 10 wt. % to 20 wt. %, and the balance is at least one of cobalt and iron.

13. The device of claim 8, wherein the implantable medical device is a cardiac function management system.

14. An electrode for use with an implantable medical device, the electrode comprising:
   an alloy including:
      iridium; and
      iron; and
   a conductive oxide layer on a surface of the alloy, the conductive oxide layer including iridium oxide and having a thickness between 5 nanometers and 2000 nanometers, wherein the alloy is cobalt-free.

15. The electrode of claim 14, wherein the alloy includes the iridium in an amount from 10 wt. % to 60 wt. %, and the balance is iron.

16. The electrode of claim 14, wherein the alloy further includes chromium and the conductive oxide layer further includes chromium oxide.

17. The electrode of claim 16, wherein the alloy includes the iridium in an amount from 10 wt. % to 50 wt. %, the chromium in an amount from 10 wt. % to 20 wt. %, and the balance is iron.

18. The electrode of claim 14, wherein the conductive oxide layer has a thickness between 10 nanometers and 1000 nanometers.

* * * * *